United States Patent [19]
Holley

[11] Patent Number: 4,863,868
[45] Date of Patent: Sep. 5, 1989

[54] APPARATUS FOR DETECTING THE PRESENCE OF MICRO ORGANISM IN LIQUID

[75] Inventor: John E. F. Holley, Near Westerham, England

[73] Assignee: Prolitec Aktiengesellschaft, Furstentum, Liechtenstein

[21] Appl. No.: 205,587

[22] Filed: Jun. 13, 1988

Related U.S. Application Data

[63] Continuation of Ser. No. 95,589, Sep. 11, 1987, abandoned, which is a continuation-in-part of Ser. No. 924,200, Oct. 28, 1986, abandoned, which is a continuation of Ser. No. 636,491, Aug. 1, 1984, abandoned.

[51] Int. Cl.$^4$ ............................................. C12M 1/28
[52] U.S. Cl. ..................................... 435/294; 435/292; 435/291
[58] Field of Search ........................ 435/291, 294, 292

[56] References Cited

U.S. PATENT DOCUMENTS

| | | | |
|---|---|---|---|
| 3,547,781 | 12/1970 | Guigan et al. | 435/292 |
| 3,765,841 | 10/1973 | Paulson et al. | 435/291 |
| 3,773,426 | 11/1973 | Mudd | 435/291 |
| 4,072,578 | 2/1978 | Cady et al. | 435/291 |
| 4,085,006 | 4/1978 | Mindick et al. | 435/291 |
| 4,128,456 | 12/1978 | Lee et al. | 435/291 |
| 4,160,205 | 7/1979 | Hobbs et al. | 435/30 |
| 4,198,482 | 4/1980 | Homer | 435/292 |
| 4,204,037 | 5/1980 | Frasch et al. | 435/291 |
| 4,209,586 | 6/1980 | Noller | 435/291 |
| 4,528,270 | 7/1985 | Matsunaga | 435/39 |

*Primary Examiner*—Carroll B. Dority, Jr.
*Attorney, Agent, or Firm*—Morgan & Finnegan

[57] ABSTRACT

An analyzer for detecting and measuring microorganisms in liquids comprising a probe with an orifice adapted to have liquid containing particles passed through it, and a means for passing cleansing liquid over the orifice is disclosed.

4 Claims, 2 Drawing Sheets

APPARATUS FOR DETECTING THE PRESENCE OF MICRO ORGANISM IN LIQUID

CROSS REFERENCE TO OTHER APPLICATIONS

This is a continuation of co-pending application Ser. No. 07/095,589, filed on Sept. 11, 1989, now abandoned, which is a continuation in part of application Ser. No. 06/924,200 filed on Oct. 28, 1986, which is a continuation of application Ser. No. 636,491 filed on Aug. 1, 1984 now abandoned.

BACKGROUND OF THE INVENTION

This invention relates to equipment for detecting and measuring microorganisms in liquids. The equipment is particularly useful for detecting microorganisms such as white and red blood cells in urine.

A known method for detection of microorganisms in urine is to incubate a sample and then detect microorganisms using conventional techniques. The process is time consuming as it needs to be done on an individual basis and requires the use of skilled staff both to carry out the test and to interpret the results.

Particle counters of the Coulter Counter type may be used to detect particles in liquids as described in the Journal of Chemical Pathology, Vol. 32, pps 386–390 (1979 Published by the BMA, London, England). In some counters liquid is drawn through an orific into the counter and the particles counted across the orifice. We have found that in some biomedical applications small orifices which give good sensitivity are prone to become blocked by debris and that larger orifices lack sensitivity.

For example it has been found that when orifices are of a size, e.g. 30–50 micrometers, they can be blocked. The orifice can be made larger e.g. at least 50 micrometers or preferably at least 100 micrometers. A larger orifice, however, can reduce sensitivity.

SUMMARY OF THE INVENTION

Figure 1:
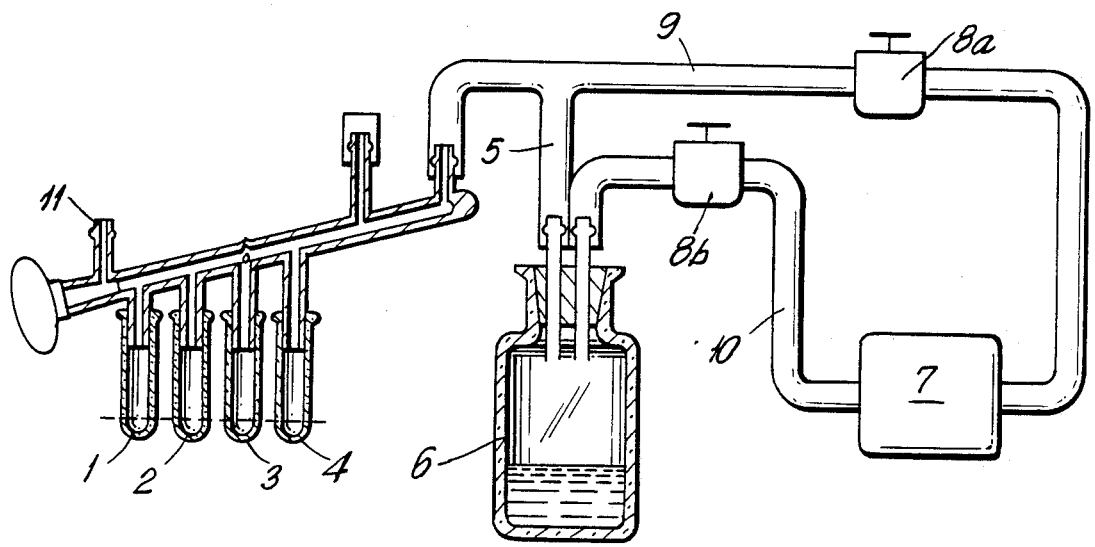
FIG. 1 is a schematic representation of a series of probes of an embodiment of the present invention.

According to the invention there is provided a probe for use in particle size distribution analyzers which probe has an orifice in its lower portion adapted to have liquid containing particles passed through it. A cleansing liquid passing means is adapted to pass cleansing liquid over said orifice to remove any materials blocking the said orifice.

In one embodiment of the invention, there is a cleansing liquid passing means on the inside and outside of the probe to clear blocking particles on either side. The cleansing liquid preferably is water but may be any liquid. The rate of flow of cleansing liquid is not critical as long as it is adequate to remove the Particles or other debris blocking the orifice. Preferably, any blockage is automatically detected and removed.

The flow of cleansing liquid over the orifice is preferably carried out automatically after each sample of liquid to be analyzed is drawn through the orifice. Back-pressure can be applied by means of a pump to force blocking particles out of the orifice.

In an embodiment of the invention the cleansing liquid to be passed over the orifice is contained in a sterile container and pumped via a pump to two tubes, one leading to the inside of the probe and one to the outside. Preferably there is an automatic valve in each tube.

A means to interpret the results can be a standard particle counter as described above and in the above referred to reference the results are obtained in the form of a graph, e.g. particle/volume distribution profile.

In the types of particle counter in which the capacitance of a liquid between two electrodes is measured and variations in this value used to determine the size of particles, normally the greater the "signal to noise" ratio the better.

In this type of detector the capacitance of the liquid between two electrodes can be measured and variations in this value can be used to determine the number and size of the particles. The shorter the path length, the lower the impedance of the counter in use and the greater the "signal to noise" ratio. This allows smaller size particles to be detected.

We have now devised an improvement which comprises forming a larger hole in the probe tube e.g. of diameter 1.5 mm to 2 mm, and fixing or gluing a thin glass slice or plate with the appropriate size orifice over the hole in the tube. By this means the diameter of the orifice used can be controlled with greater accuracy.

In one embodiment, the electrodes are made of platinum and formed or melted into the glass probe which because of the thinness of the glass slice means the path length between the electrodes is reduced. The glass slice or plate can be fixed by gluing with an appropriate adhesive and it may be necessary to grind the tube flat round the hole before fixing the plate. By this means a shorter path length between the electrodes can be obtained.

Equipment can also be provided for detecting the presence of cell-size particles in a liquid, which equipment comprises a multi-well plate support means and one or more counting devices capable of counting and sizing particles in liquids, each of the counting devices measuring the capacitance of liquids and having an electrical output and also comprising a probe capable of being inserted in a well in a multi-well plate, said counting devices being positioned above the multi-well plate support means in a row corresponding substantially to a row of wells in a multi-well plate there being inserting means capable of raising and lowering the counting devices simultaneously relative to the multi-well plate support means and moving means capable of moving the row of counting devices and multi-well plate support means substantially laterally relative to devices and multi-well plate support means moved relative to each other so as to position the counting devices above another row of wells in said multi-well plate.

Each particle size distribution analyzer is preferably of a size to fit into a well in a specially molded multi-well plate. The plate, for example, may be in the form of a probe. The means to remove a sample from a well in said multi-well plate is preferably a suction means connected to the counter and activated by movement thereof so that when the probe enters glass tube forming part of the counter, the suction means is activated to suck the right amount of sample into the probe.

In the equipment of the present invention, the results from each particle distribution analyzer are preferably fed into a microprocessor for interpretation and read out. Before being fed to the microprocessor, the outputs from the analyzer are preferably amplified using an a.c. amplifying circuit or restricted band width, i.e. one having a frequency response of which does not extend to very low frequencies. Because the particle size distribution analyzer can detect different size particles, it is possible by use of the microprocessor for a population of different size particles to be analyzed, compared with a standard negative cell distribution profile, and for any deviation generate a positive result. Positive results may be compared to a series of known particle size distribution profiles to identify the microorganisms present. The results can be plotted in analogue form or as a biogram and a hard copy produced. The same microprocessor can also coordinate and control the mechanical and electrical operations of the equipment.

The equipment of the invention enables an analysis of cell population to be quickly and automatically obtained.

An advantage of the equipment of the invention is that it enables a quick reading to be obtained which enables the population distribution to be detected. By this time the cell volume distribution can be analyzed, which enables preliminary categorisation of the type of infecting organism

DETAILED DESCRIPTION OF THE PREFERRED EMBODIMENTS

Figure 2:
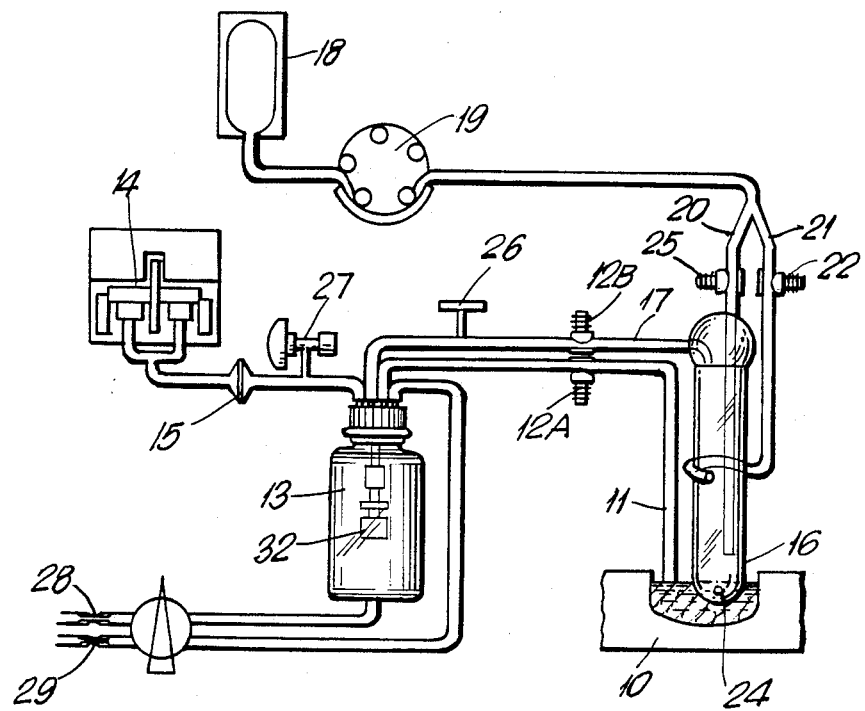
FIG. 2 is a schematic representation of one embodiment of a probe of the present invention having cleansing liquid means.

FIG. 1 shows schematically a group or probes,

FIG. 2 shows a single probe with cleansing liquid dispensing means and

Figure 3:
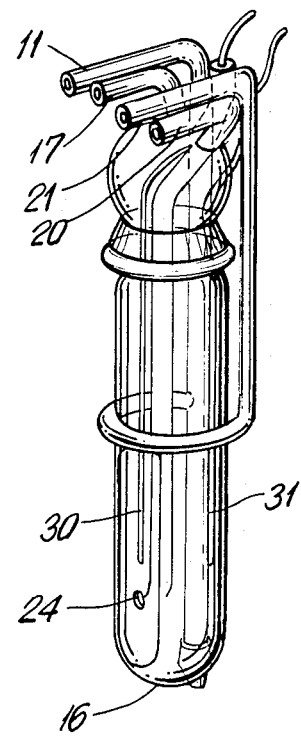
FIG. 3 is a perspective view of a probe of the present invention.

FIG. 3 is a perspective view of the probe of FIG. 2.

Referring to FIG. 1, the liquid removal system is shown in which particle size distribution analyzers in the form of Probes 1, 2, 3 and 4, a tube 5 for carrying liquid, a residue discharge vessel 6, a vacuum pump 7, three-way valves 8a and 8b and air tubes 9 and 10 are provided.

In one embodiment of the invention, when probes 1-4 are immersed in liquid, valve 8a is closed and pump 7 generates suction which causes liquid to enter the probes. By closing valve 8b the liquid is held in the probe for sufficient time to analyze the liquid. By opening valve 8b the liquid is sucked into vessel 6 for discharge. Air line 9 is used to blow air and clean the probes. Inlet port 11 is used to fill the system from a clean liquid source.

When the liquid is in the probe, the analyzer measures the number and size of particles in the liquid.

Referring to FIG. 2, well 10 contains particle containing liquid. Drain tube 11 having valve 12A is connected to residue vessel 13 containing level sensor 32 to which vessel 13 is connected vacuum pump 14 and vacuum regulator 27 via filter 15. Probe 16 is connected via tube 17 having pressure sensor 26 and valve 12B to residue vessel 13. There is in addition a cleansing liquid storage container 18 connected via pump 19 to tubes 20 and 21 and valves 22 and 25 to the inside and outside of probe 16.

In use, liquid is sucked from well 10 through orifice 24 into probe 16. The liquid is analyzed for particles and the cleansing liquid is passed from container 18 and one or more tubes 20 and 21 over orifice 24 to clear any debris. Valves 12A, 12B, 25, and 22 are all controlled to make the entire process automatic. There is an empty port 28 and fill port 29 connected to vessel 13. If required back-pressure via tube 20 can free particles blocking orifice 24.

Referring to FIG. 3, probe 16 is shown with a drain tube 11 on the outside of probe 16. On the inside and outside of probe 16 are tubes 20 and 21. Also connected to the inside of probe 16 is tube 17. Probe 16 also has an orifice 24.

In FIG. 3 the electrodes 30 and 31 are shown in position in the probe.

What is claimed is:

1. A particle size distribution analyzer comprising a probe having an orifice in its lower portion and means adapted to draw liquid containing particles through said orifice into said probe, and a cleansing liquid means adapted to pass liquid under positive pressure through said orifice to remove any material blocking said orifice.

2. An analyzer as claimed in claim 1 having liquid passing means for passing cleansing liquid over the inside and outside of the orifice.

3. An analyzer as claimed in claim 1 in which orifice size is about 1 mm to about 50 mm.

4. An Analyzer as claimed in claim 1 in which orifice size is about 3 mm to about 50 mm.

* * * * *